(12) United States Patent
Chen

(10) Patent No.: US 12,724,029 B2
(45) Date of Patent: Sep. 1, 2026

(54) CONCENTRATION DETERMINATION METHOD

(71) Applicant: Taiwan Semiconductor Manufacturing Company, Ltd., Hsinchu (TW)

(72) Inventor: Tung-Tsun Chen, Hsinchu City (TW)

(73) Assignee: Taiwan Semiconductor Manufacturing Company, Ltd., Hsinchu (TW)

( * ) Notice: Subject to any disclaimer, the term of this patent is extended or adjusted under 35 U.S.C. 154(b) by 1065 days.

(21) Appl. No.: 17/736,105

(22) Filed: May 4, 2022

(65) Prior Publication Data

US 2023/0358745 A1 Nov. 9, 2023

(51) Int. Cl.

*G01N 33/569* (2006.01)
*C12Q 1/70* (2006.01)
*G01N 27/414* (2006.01)

(52) U.S. Cl.

CPC ....... *G01N 33/56983* (2013.01); *C12Q 1/701* (2013.01); *G01N 27/4145* (2013.01); *G01N 27/4148* (2013.01); *C12Q 2600/118* (2013.01)

(58) Field of Classification Search

CPC ......... G01N 33/56983; G01N 27/4145; G01N 27/4148; C12Q 1/701; C12Q 2600/118

See application file for complete search history.

(56) References Cited

U.S. PATENT DOCUMENTS 9,689,835 B2 6/2017 Liu et al.
9,709,524 B2 7/2017 Liu et al.

(Continued)

OTHER PUBLICATIONS

Yang et al., Qualitative immunoassay for the detection of anti-SARS-COV-2 spike antibody in human milk samples, STAR Protocols , 2022, 3, 101203 (Year: 2022).*

(Continued)

*Primary Examiner* — Shizhi Qian
(74) *Attorney, Agent, or Firm* — JCIPRNET

(57) ABSTRACT

A concentration determination method includes the following steps. A sample fluid having a target material therein is diluted with a $1^{st}$ dilution factor to an $N_{th}$ dilution factor to form a $1^{st}$ sample to an $N^{th}$ sample. A bio-sensing integrated circuit having a $1^{st}$ assay to an $N^{th}$ assay is provided. The $1^{st}$ sample to the $N^{th}$ sample are respectively applied to the $1^{st}$ assay to the $N^{th}$ assay. A bio-sensing process is performed on the $1^{st}$ sample to the $N^{th}$ sample to obtain a $1^{st}$ measurement value to an $N^{th}$ measurement value. The $1^{st}$ measurement value to the $N^{th}$ measurement value are compared with a threshold value to determine a threshold dilution factor, which corresponds to a largest dilution factor that has a measurement value higher than the threshold value. A concentration of the target material is calculated based on the threshold dilution factor and a limit of detection.

20 Claims, 9 Drawing Sheets

(56) References Cited

U.S. PATENT DOCUMENTS

| | | | | |
|---|---|---|---|---|
| 2016/0334362 | A1* | 11/2016 | Liu | H10N 19/00 |
| 2018/0203006 | A1* | 7/2018 | Huang | C12Q 1/6837 |
| 2021/0102265 | A1* | 4/2021 | Wu | C12Q 1/70 |
| 2021/0325339 | A1 | 10/2021 | Chen et al. | |
| 2024/0272159 | A1* | 8/2024 | Muthuswamy | G01N 33/5438 |

OTHER PUBLICATIONS

Lim et al., Emerging Biosensors to Detect Severe Acute Respiratory Syndrome Coronavirus 2 (SARS-CoV-2): A Review, Biosensors, 2021, 11, 434 (Year: 2021).*

Spitz et al. 2020 White Paper on Recent Issues in Bioanalysis: BAV Guidance, CLSI H62, Biotherapeutics Stability, Parallelism Testing, CyTOF and Regulatory Feedback, Bioanalysis, 2021, 13, 295-361 (Year: 2021).*

Martins et al., Addressing the Theoretical and Experimental Aspects of Low-Dimensional-Materials-Based FET Immunosensors: A Review, Chemosensors, 2021, 9, 162 (Year: 2021).*

Seo et al., Rapid Detection of COVID-19 Causative Virus (SARS-CoV-2) in Human Nasopharyngeal Swab Specimens Using Field-Effect Transistor-Based Biosensor, ACS Nano, 2020, 14, 5135-5142 (Year: 2020).*

* cited by examiner

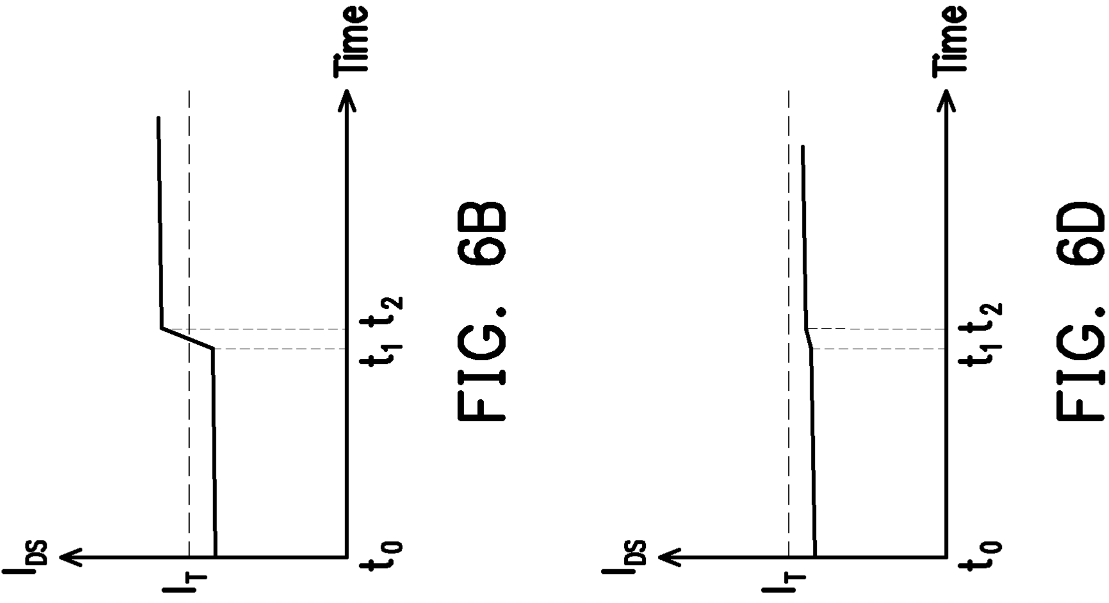
FIG. 6B
FIG. 6D
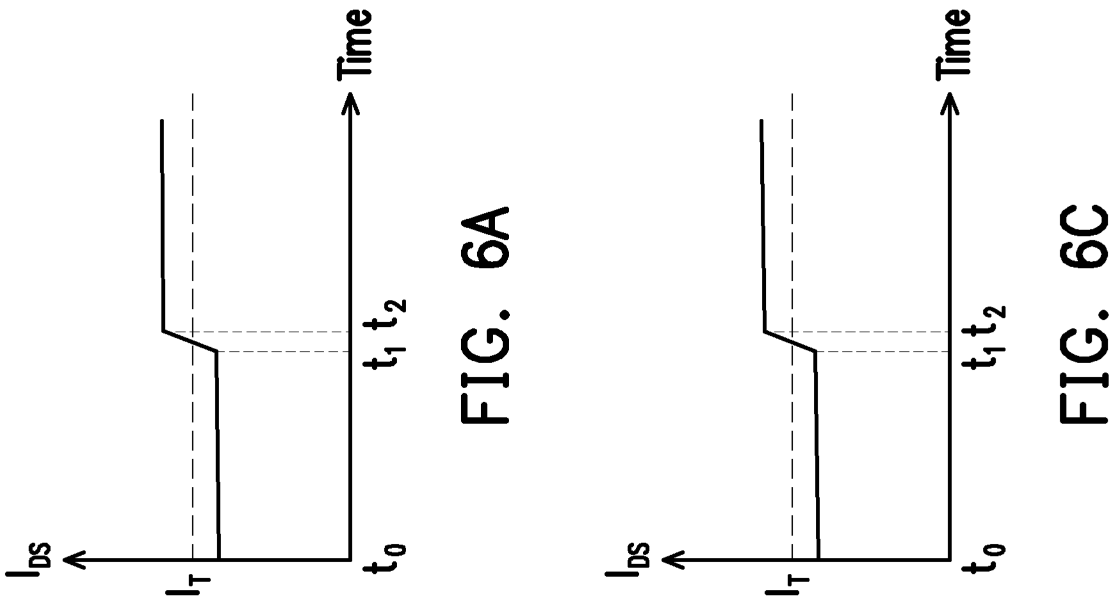
FIG. 6A
FIG. 6C

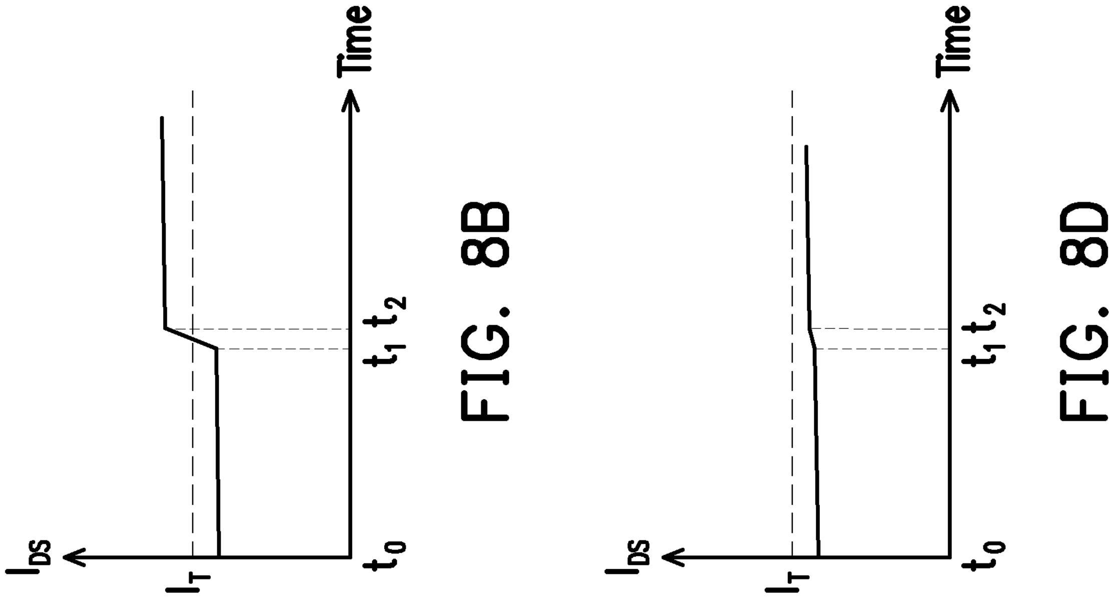
FIG. 8B
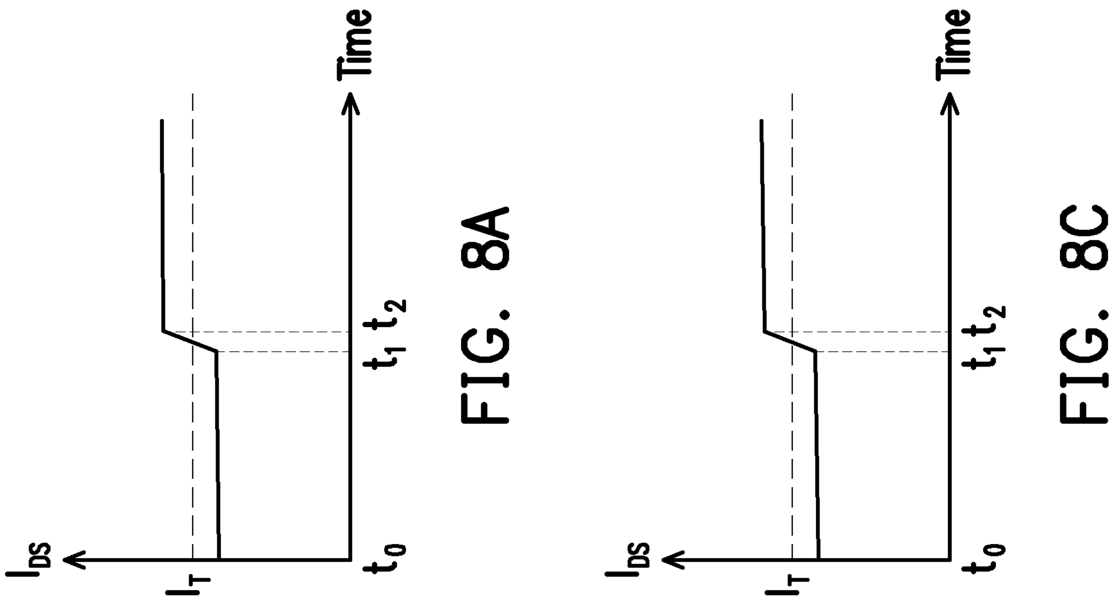
FIG. 8A
FIG. 8D
FIG. 8C

CONCENTRATION DETERMINATION METHOD

BACKGROUND

Biosensors are devices for sensing and detecting biomolecules and operate on the basis of electronic, electrochemical, optical, and mechanical detection principles. Biosensors that include transistors are sensors that electrically sense charges, photons, and mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert electric signals, and can be easily applied to integrated circuits (ICs).

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

FIG. 6A is a current vs. time curve of the first sample in the concentration determination method of FIG. 5.

FIG. 6B is a current vs. time curve of the second sample in the concentration determination method of FIG. 5.

FIG. 6C is a current vs. time curve of the third sample in the concentration determination method of FIG. 5.

FIG. 6D is a current vs. time curve of the fourth sample in the concentration determination method of FIG. 5.

FIG. 8A is a current vs. time curve of the first sample in the concentration determination method of FIG. 7.

FIG. 8B is a current vs. time curve of the second sample in the concentration determination method of FIG. 7.

FIG. 8C is a current vs. time curve of the third sample in the concentration determination method of FIG. 7.

FIG. 8D is a current vs. time curve of the fourth sample in the concentration determination method of FIG. 7.

DETAILED DESCRIPTION

Figure 1:
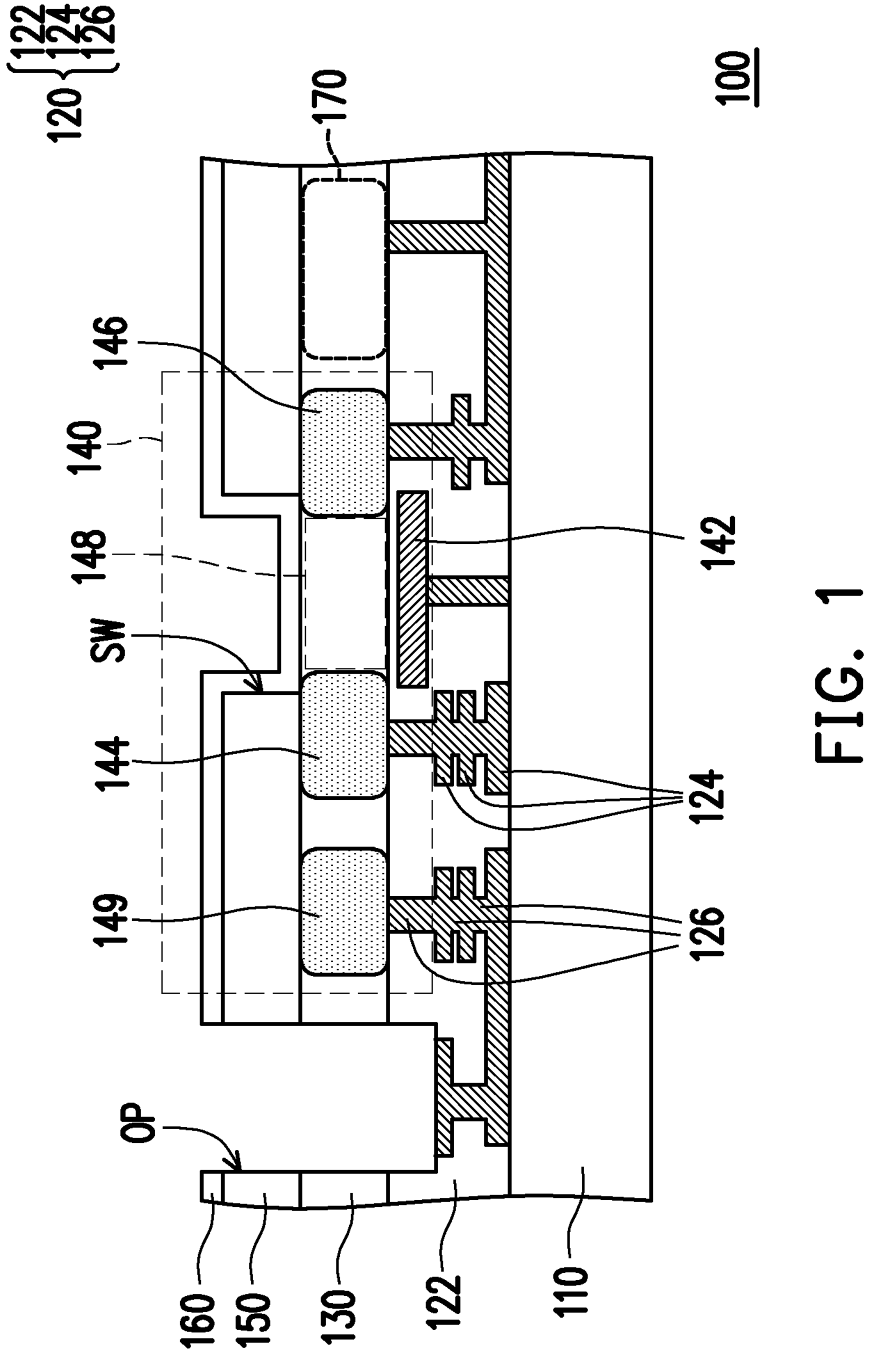
FIG. 1 is a schematic cross-sectional view of a bio-sensing integrated circuit in accordance with some embodiments of the disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 1 is a schematic cross-sectional view of a bio-sensing integrated circuit 100 in accordance with some embodiments of the disclosure. Referring to FIG. 1, the bio-sensing integrated circuit 100 includes a carrier substrate 110, an interconnect structure 120, a semiconductor substrate 130, a Biosensor Field-Effect Transistor (BioFET) 140, a passivation layer 150, a sensing layer 160, and a circuitry 170.

In some embodiments, the carrier substrate 110 is a bulk semiconductor substrate, such as a bulk substrate of monocrystalline silicon. As illustrated in FIG. 1, the interconnect structure 120 is disposed on the carrier substrate 110. In some embodiments, the interconnect structure 120 includes a dielectric layer 122, a plurality of conductive patterns 124, and a plurality of conductive vias 126. In some embodiments, a material of the dielectric layer 122 includes polyimide, epoxy resin, acrylic resin, phenol resin, benzocyclobutene (BCB), polybenzooxazole (PBO), or any other suitable polymer-based dielectric material. Alternatively, the dielectric layer 122 may be formed of oxides or nitrides, such as silicon oxide, silicon nitride, aluminum oxide, hafnium oxide, hafnium zirconium oxide, or the like. The dielectric layer 122 may be formed by suitable fabrication techniques, such as spin-on coating, chemical vapor deposition (CVD), plasma-enhanced chemical vapor deposition (PECVD), or the like. For simplicity, the dielectric layer 122 is illustrated as a bulky layer in FIG. 1, but it should be understood that the dielectric layer 122 may be constituted by multiple dielectric layers. In some embodiments, the conductive patterns 124 and the conductive vias 126 are embedded in the dielectric layer 122. In some embodiments, the conductive patterns 124 located at different level heights are connected to one another through the conductive vias 126. In other words, the conductive patterns 124 are electrically connected to one another through the conductive vias 126. In some embodiments, a material of the conductive patterns 124 and the conductive vias 126 includes aluminum, titanium, copper, nickel, tungsten, or alloys thereof. The conductive patterns 124 and the conductive vias 126 may be formed by electroplating, deposition, and/or photolithography and etching. In some embodiments, the conductive patterns 124 and the conductive vias 126 are formed simultaneously. It should be noted that the number of the conductive patterns 124 and the number of the conductive vias 126 illustrated in FIG. 1 are merely for illustrative purposes, and the disclosure is not limited thereto. In some alternative embodiments, fewer or more layers of the conductive patterns 124 and/or the conductive vias 126 may be formed depending on the circuit design. In some embodiments, the interconnect structure 120 is referred to as "back-end-of-line (BEOL) interconnect structure."

In some embodiments, the semiconductor substrate 130 is disposed on the interconnect structure 120. The semiconductor substrate 130 accommodates the BioFET 140 and may be, for example, a semiconductor layer of a semiconductor-on-insulator (SOI) substrate or a bulk semiconductor substrate.

As illustrated in FIG. 1, the BioFET 140 includes a gate electrode 142, a source region 144, a drain region 146, a channel region 148, and a body region 149. In some embodiments, the gate electrode 142 is embedded in the interconnect structure 120. Moreover, the gate electrode 142 is electrically connected to the interconnect structure 120. For example, the gate electrode 142 is in physical contact with some of the conductive vias 126 such that the gate electrode 142 is electrically connected to the conductive patterns 124 and the conductive vias 126 of the interconnection structure 120. In some embodiments, a material of the gate electrode 142 includes polysilicon, metal, metal alloy, or a combination thereof. As illustrated in FIG. 1, the source region 144 and the drain region 146 are embedded in the semiconductor substrate 130. The source region 144 and the drain region 146 may be respectively doped with p-type dopants, such as boron or $BF_2$; n-type dopants, such as phosphorus or arsenic; and/or a combination thereof. In some embodiments, the source region 144 and the drain region 146 are electrically connected to the interconnect structure 120. For example, the source region 144 and the drain region 146 are in physical contact with some of the conductive vias 126 such that the source region 144 and the drain region 146 are electrically connected to the conductive patterns 124 and the conductive vias 126 of the interconnection structure 120. In some embodiments, the channel region 148 is also embedded in the semiconductor substrate 130. For example, the source region 144 and the drain region 146 may respectively locate on two opposite sides of the channel region 148. In some embodiments, the channel region 148 is a doped region. For example, the channel region 148 may be doped with p-type dopants, such as boron or $BF_2$; n-type dopants, such as phosphorus or arsenic; and/or a combination thereof. In some embodiments, the doping type of the channel region 148 is different from the doping type of the source region 144 and the drain region 146. In some embodiments, the source region 144, the drain region 146, and the channel region 148 extend continuously from a top surface of the semiconductor substrate 130 to a bottom surface of the semiconductor substrate 130. On the other hand, the gate electrode 142 is arranged under the semiconductor substrate 130. In some embodiments, the gate electrode 142 is arranged laterally between the source region 144 and the drain region 146, and is spaced apart from the semiconductor substrate 130 by a gate dielectric layer (not shown).

In some embodiments, the body region 149 is adjacent to the source region 144. For example, the body region 149 is embedded in the semiconductor substrate 130. In some embodiments, the body region 149 is electrically connected to the interconnect structure 120. For example, the body region 149 is in physical contact with some of the conductive vias 126 such that the body region 149 is electrically connected to the conductive patterns 124 and the conductive vias 126 of the interconnection structure 120. In some embodiments, the body region 149 is used to bias the carrier concentration in the channel region 148. As such, a negative voltage bias may be applied to the body region 149 to improve the sensitivity of the BioFET 140. In some embodiments, the body region 149 is electrically grounded. However, the disclosure is not limited thereto. In some alternative embodiments, the body region 149 is electrically connected to the source region 144.

As illustrated in FIG. 1, the passivation layer 150 is disposed over the semiconductor substrate 130. In some embodiments, the passivation layer 150 includes a sensing well SW. The sensing well SW extends into the passivation layer 150 to proximate the channel region 148. For example, the sensing well SW extends through the passivation layer 150 to expose the channel region 148. In some embodiments, the passivation layer 150 includes, for example, silicon dioxide, a buried oxide (BOX) layer of a SOI substrate, some other dielectrics, or a combination thereof.

In some embodiments, the sensing layer 160 is disposed on the passivation layer 150. For example, the sensing layer 160 covers the passivation layer 150 and extends into the sensing well SW to be in physical contact with the channel region 148. In some embodiments, the sensing layer 160 is configured to react with or bind to bio-entities to facilitate a change in the conductance of the channel region 148, such that the presence of the bio-entities may be detected based on the conductance of the channel region 148. In some embodiments, a material of the sensing layer 160 includes hafnium oxide, titanium nitride, titanium, a high-k dielectric, some other materials configured to react with or bind to the bio-entities, or a combination thereof. In some embodiments, the high-k dielectric is a dielectric with a dielectric constant that is greater than about 3.9. The bio-entities may be, for example, DNA, ribonucleic acid (RNA), drug molecules, enzymes, proteins, antibodies, antigens, or a combination thereof. In some embodiments, the sensing layer 160 has a thickness of less than about 100 nm.

In some embodiments, the circuitry 170 is embedded in the semiconductor substrate 130 and is adjacent to the drain region 146. In some embodiments, the circuitry 170 is separated from the drain region 146. In some embodiments, the circuitry 170 includes any number of Metal-Oxide-Semiconductor Field-Effect Transistor (MOSFET) devices, resistors, capacitors, or inductors to form circuitry to aid in the operation of the bio-sensing integrated circuit 100. In some embodiments, the circuitry 170 may be optional.

As illustrated in FIG. 1, the bio-sensing integrated circuit 100 further includes a pad opening OP. In some embodiments, the pad opening OP penetrates through the sensing layer 160, the passivation layer 150, and the semiconductor substrate 130. In some embodiments, the pad opening OP further extend into a portion of the interconnect structure 120. For example, the pad opening OP penetrate through a portion of the dielectric layer 122 to expose one of the topmost conductive patterns 124.

For simplicity, one BioFET 140 and one sensing well SW is shown in FIG. 1. However, it should be understood that multiple BioFETs 140 and multiple sensing wells SW may be found in the bio-sensing integrated circuit 100. When multiple BioFETs 140 and multiple sensing wells SW are presented in the bio-sensing integrated circuit 100, the sensing wells SW may be arranged to match the corresponding BioFET 140. For example, each sensing well SW may correspond to one BioFET 140. However, the disclosure is not limited thereto. In some alternative embodiments, each sensing well SW may have multiple BioFETs 140 directly underneath it. In some embodiments, a plurality of shallow trench isolation (STI) regions (not shown) may be embedded in the semiconductor substrate 130 to isolate two adjacent BioFETs 140.

Figure 2:
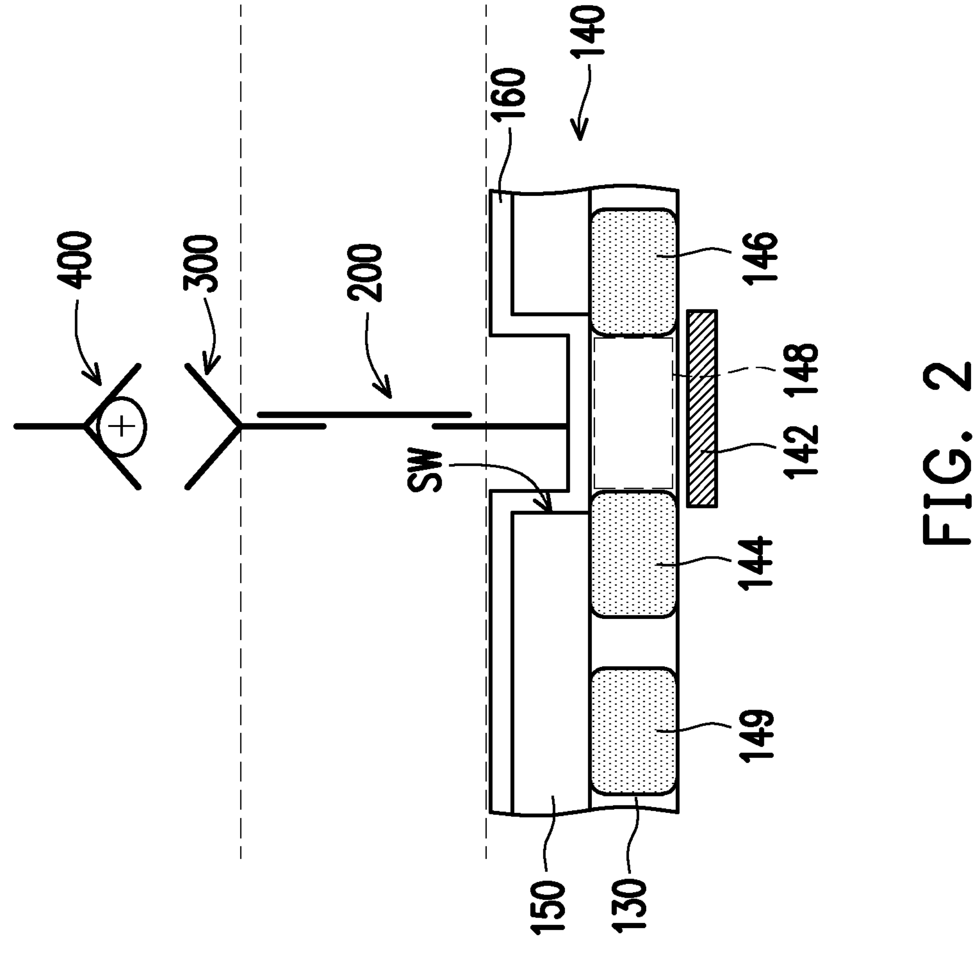
FIG. 2 is a schematic partial enlarged view of the bio-sensing integrated circuit in FIG. 1 during a bio-sensing process.

FIG. 2 schematic partial enlarged view of the bio-sensing integrated circuit 100 in FIG. 1 during a bio-sensing process. Referring to FIG. 2, a cross-linker 200 is provided on the sensing layer 160. In some embodiments, a probe 300 is attached to the cross-linker 200 for capturing a target material 400. Please be noted that the drawings shown in FIG. 2 is not to scale, and in some embodiments, the cross-linker 200 and the probe 300 are provided within the sensing well SW. Referring to FIG. 1 and FIG. 2, during the bio-sensing process, a sample fluid (not shown) is provided on the bio-sensing integrated circuit 100. For example, the sample fluid flows into the sensing well SW such that the target material 400 in the sample fluid is bind to the probe 300. Due to the binding between the target material 400 and the probe 300, the conductance of the channel region 148 underneath the sensing well SW would change. As such, the presence of the target material 400 may be detected based on the conductance of the channel region 148.

In some embodiments, the probe 300 includes Protein-based probe, DNA-based probed, Peptide-based probe, and/or Aptamer-based probe. The Protein-based probe includes SARS-CoV-2 Spike Antibody and SARS-CoV-2 Spike Antigen. The DNA-based probe includes SARS-CoV-2 Complementary DNA. The Peptide-based probe includes SARS-CoV-2-Complementary Peptide. The Aptamer-based probe includes SARS-CoV-2 Complementary Aptamer.

In some embodiments, the target material 400 includes SAS-CoV-2 Antigen, SARS-CoV-2 Antibody, and SARS-CoV-2 RNA. In some embodiments, these target materials 400 correspond to the probes 300 listed above. For example, the SARS-CoV-2 Antigen corresponds to SARS-CoV-2 Spike Antibody and SARS-CoV-2 Complementary Peptide. The SARS-CoV-2 Antibody corresponds to SARS-CoV-2 Spike Antigen. The SARS-CoV-2 RNA corresponds to SARS-CoV-2 Complementary DNA and SARS-CoV-2 Complementary Aptamer.

Figure 3A:
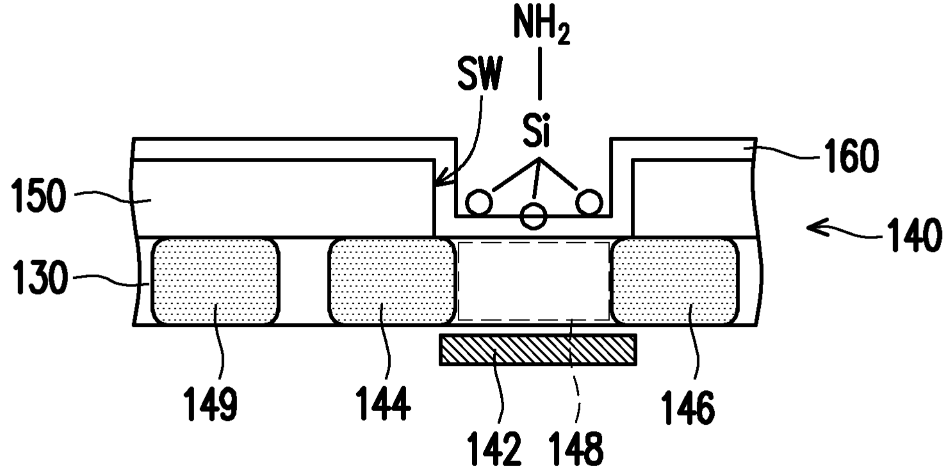
FIG. 3A to FIG. 3C are schematic views of various cross-linkers attaching to the sensing layer of the bio-sensing integrated circuit in FIG. 1.
Figure 3B:
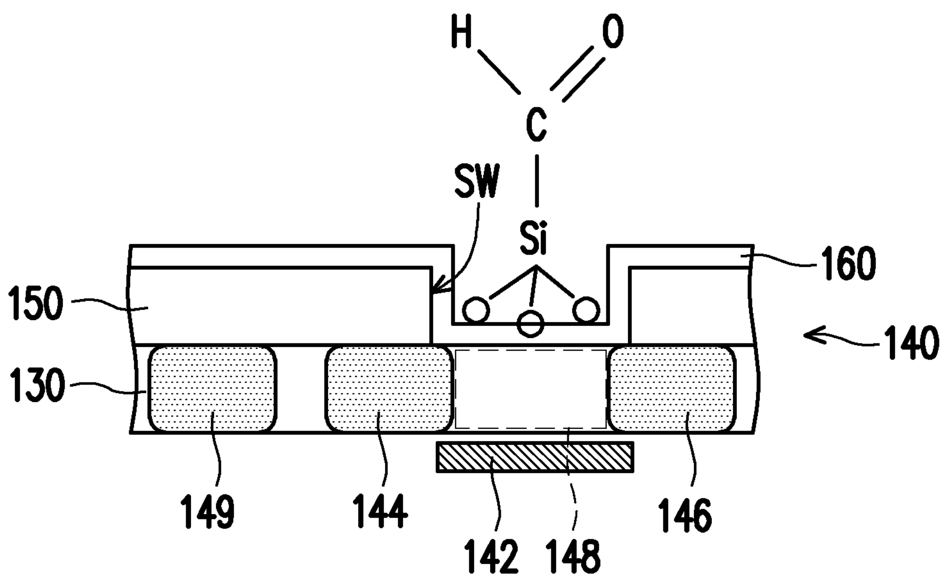
Figure 3C:
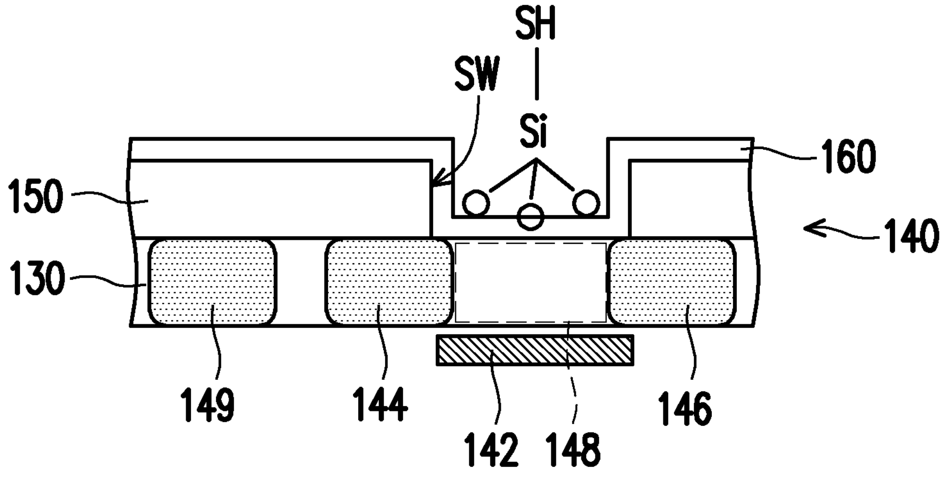

In some embodiments, the cross-linker 200 includes a combination of an amino group and a silane group, a combination of an aldehyde group and a silane group, or a combination of a thiol group and a silane group. The molecular structures of various cross-linkers 200 are shown in FIG. 3A to FIG. 3C. FIG. 3A to FIG. 3C are schematic views of various cross-linkers 200 attaching to the sensing layer 160 of the bio-sensing integrated circuit 100 in FIG. 1. Referring to FIG. 3A, amino silanization in which an amino group binding to a silane group is shown. Referring to FIG. 3B, aldehyde silanization in which an aldehyde group binding to a silane group is shown. Referring to FIG. 3C, thiol silanization in which a thiol group binding to a silane group is shown.

Figure 4:
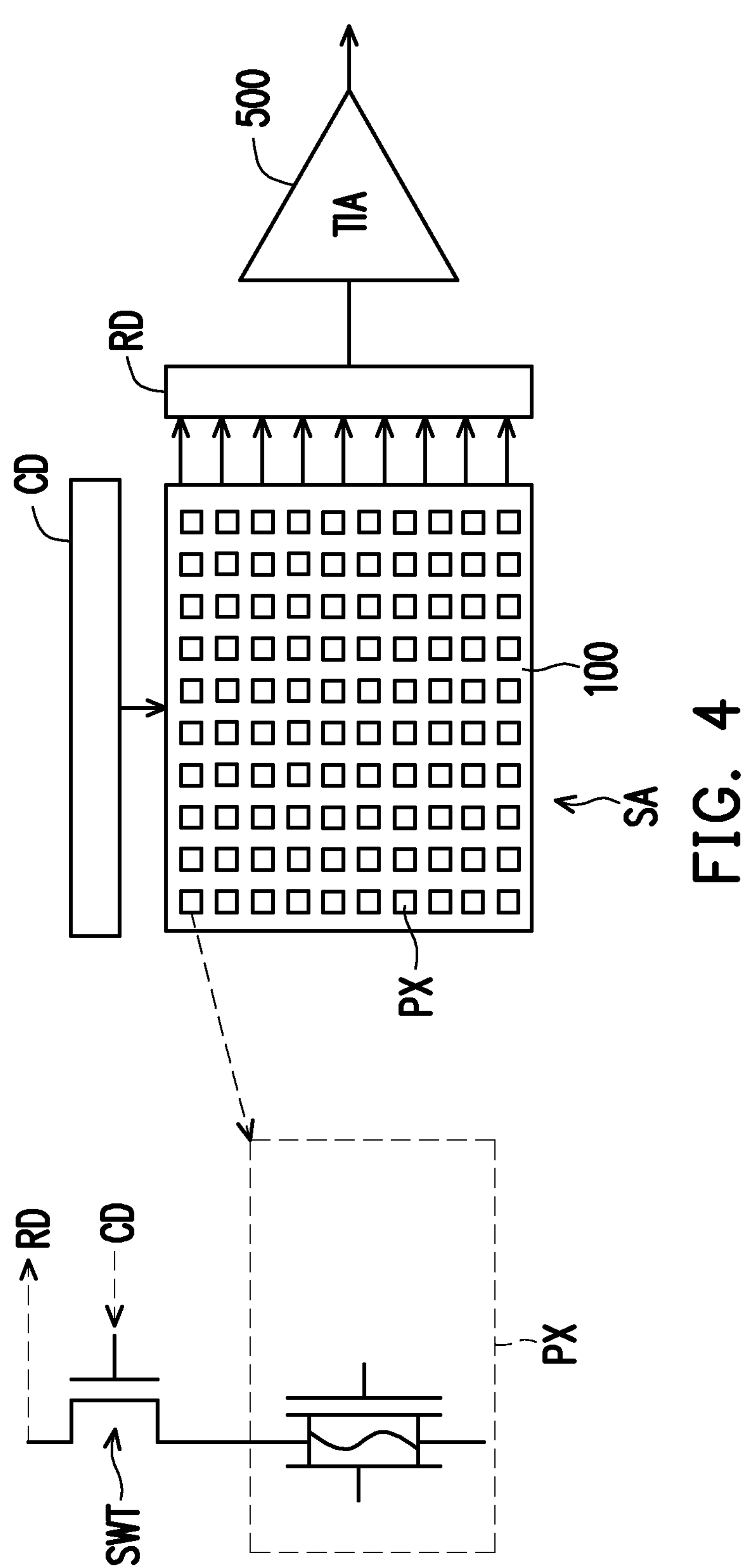
FIG. 4 is an example diagram of a sensor array and a schematic circuit diagram of the sensor array.

FIG. 4 is an example diagram of a sensor array SA and a schematic circuit diagram of the sensor array SA. In some embodiments, the sensor array SA is provided by the bio-sensing integrated circuit 100 discussed above. For example, when multiple BioFETs 140 and multiple sensing wells SW are presented in the bio-sensing integrated circuit 100, the sensing wells SW and the BioFETs 140 may be arranged in an array to form the sensor array SA of FIG. 4. As illustrated in FIG. 4, the sensor array SA includes, for example, 10 columns and 10 rows. In some embodiments, each row includes 10 pixels PX. Meanwhile, each column also includes 10 pixels PX. In some embodiments, each pixel PX corresponds to one sensing well SW and one bioFET 140 shown in FIG. 1. In some embodiments, each pixel PX in the sensor array SA corresponds to a particular column and a particular row. In some embodiments, a column decoder CD provides a column selection signal to the pixels PX in the sensor array SA, and a row decoder RD provides a row selection signal to the pixels PX in the sensor array SA. For example, a selective switch SWT corresponding to a particular pixel PX is electrically connected to both the column decoder CD and the row decoder RD. The selective switch SWT may be turned on in response to a selection signal provided by the column decoder CD and the row decoder RD, and in turn enables the bio-sensing process of the corresponding pixel PX. As illustrated in FIG. 4, the sensor array SA is electrically coupled to a Trans-impedance Amplifier (TIA) 500. In some embodiments, the measurement values (for example, a current between the source region 144 and the drain region 146) obtained from each pixel PX during the bio-sensing process are sequentially transmitted to the TIA 500. Subsequently, the TIA 500 enhances and magnifies the signal quality to improve the detection ability of the sensor array SA.

In some embodiments, the bio-sensing process may include a quantitative bio-sensing process. In some embodiments, the quantitative bio-sensing process may be adopted in a concentration determination method. For example, an initial concentration of a target material 400 in a sample fluid may be determined by the quantitative bio-sensing process. In some embodiments, the concentration determination method includes the following steps. A sample fluid having a target material 400 therein is diluted with a $1^{st}$ dilution factor to an $N^{th}$ dilution factor to respectively form a $1^{st}$ sample to an $N^{th}$ sample. For example, the $1^{st}$ sample to the $N^{th}$ sample respectively has a concentration of $1/N_1$ to $1/N^{th}$ of the sample fluid. That is, the $1^{st}$ dilution factor to the $N^{th}$ dilution factor are respectively $N_1$ to $N^{th}$. In some embodiments, the concentration decreases from the $1^{st}$ sample to the $N^{th}$ sample. That is, the $N^{th}$ dilution factor is greater than the $N^{th-1}$ dilution factor. For example, the value of $N_{th}$ is greater than the value of $N_{th-1}$. Thereafter, at least one bio-sensing integrated circuit 100 as shown in FIGS. 1 and 4 is provided. The at least one bio-sensing integrated circuit 100 may provide a $1^{st}$ assay to an $N^{th}$ assay. Then, the $1^{st}$ sample to the $N^{th}$ sample are respectively applied to the $1^{st}$ assay to the $N^{th}$ assay. Subsequently, a bio-sensing process is performed on the $1^{st}$ sample to the $N^{th}$ sample by the bio-sensing integrated circuit 100 to obtain a $1^{st}$ measurement value to an $N^{th}$ measurement value respectively for the $1^{st}$ sample to the $N^{th}$ sample. In some embodiments, the $1^{st}$ measurement value to the $N^{th}$ measurement value are currents between the source region 144 and the drain region 146. Then, the $1^{st}$ measurement value to the $N^{th}$ measurement value are compared with a threshold value (for example, a threshold current) to determine a threshold dilution factor and a threshold sample. In some embodiments, the threshold dilution factor corresponds to a largest dilution factor that has a measurement value higher than the threshold value. Meanwhile, the threshold sample corresponds to a sample that has a measurement value higher than the threshold value and has a lowest concentration. Thereafter, a concentration of the target material 400 in the sample fluid may be calculated based on the threshold dilution factor and a limit of detection of the bio-sensing integrated circuit 100 or based on the concentration of the threshold sample and a limit of detection of the bio-sensing integrated circuit 100. For example, the concentration of the target material 400 in the sample fluid is a product of the threshold dilution factor and the limit of detection of the bio-sensing integrated circuit 100. In other words, the concentration of the target material 400 in the sample fluid is a product of a reciprocal of the concentration of the threshold sample and the limit of detection of the bio-sensing integrated circuit 100.

The concentration determination method will be exemplified in detail below in conjunction with FIG. 5, FIGS. 6A-6D, FIG. 7, and FIGS. 8A-8D.

Figure 5:
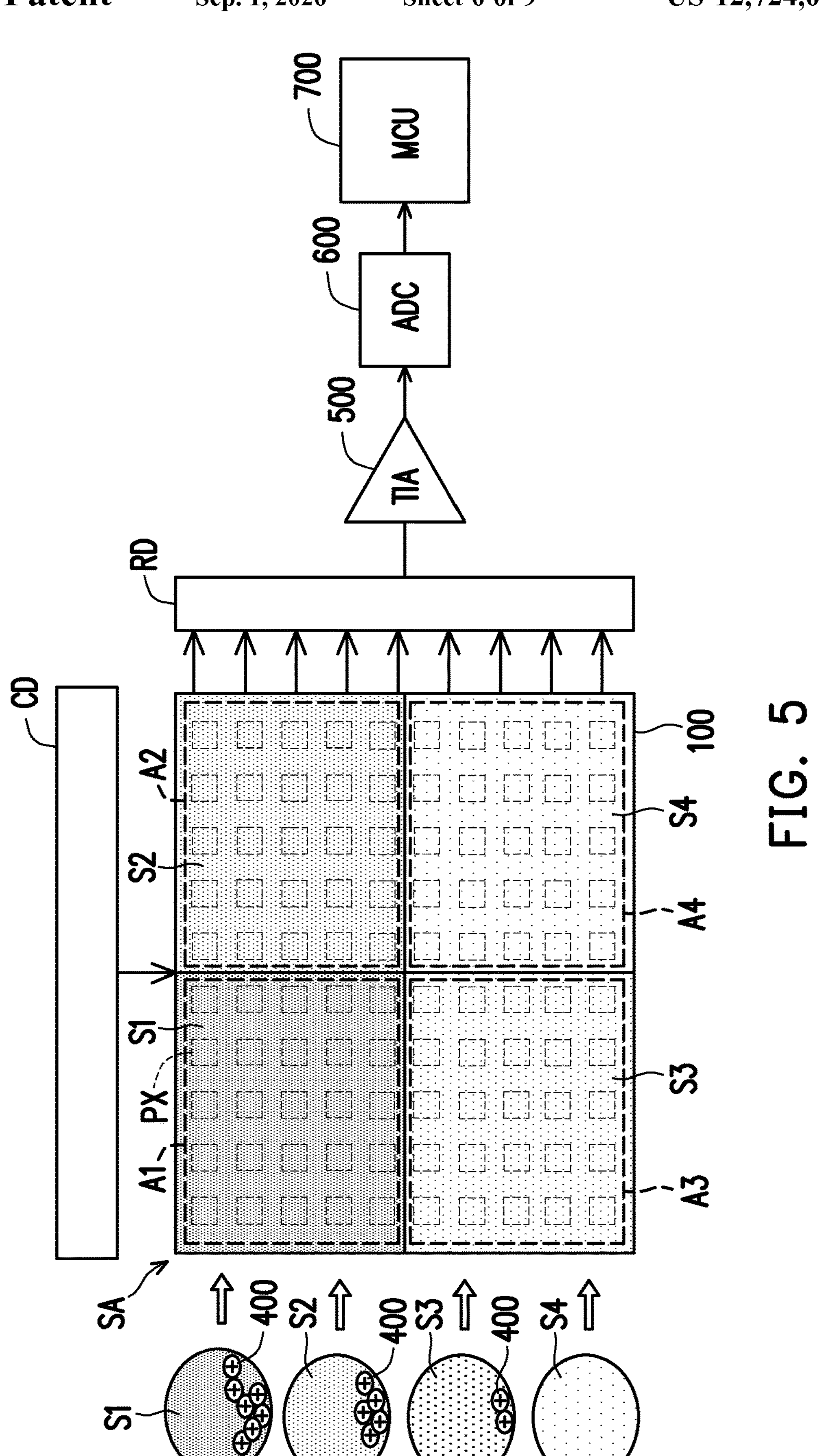
FIG. 5 is a schematic flow of a concentration determination method in accordance with some embodiments of the disclosure.

FIG. 5 is a schematic flow of a concentration determination method in accordance with some embodiments of the disclosure. Referring to FIG. 5, the sample fluid having the target material 400 therein is being diluted to form a first sample S1, a second sample S2, a third sample S3, and a fourth sample S4. In some embodiments, the dilution factor for the first sample S1 is $N_1$, the dilution factor for the second sample S2 is $N_2$, the dilution factor for the third sample S3 is $N_3$, and the dilution factor for the fourth sample S4 is $N_4$. In some embodiments, $N_1$ to $N_4$ may be any arbitrary positive number, as long as $N_1<N_2<N_3<N_4$. For ease of explanation, in the present embodiment, $N_1$ is taken as $10^1$, $N_2$ is taken as $10^2$, $N_3$ is taken as $10^4$, and $N_4$ is taken as $10^6$. For example, the first sample S1 has a concentration of 1/10 of the original sample fluid, the second sample S2 has a concentration of 1/100 of the original sample fluid, the third sample S3 has a concentration of 1/1000 of the original sample fluid, and the fourth sample S4 has a concentration of 1/1000000 of the original sample fluid. In some embodiments, the concentration of the target material 400 also reduces in proportional with respect to the dilution factor. For example, the target material 400 in the first sample S1 has a concentration of 1/10 of the original concentration, the target material 400 in the second sample S2 has a concentration of 1/100 of the original concentration, the target material 400 in the third sample S3 has a concentration of 1/10000 of the original concentration, and the target material 400 in the fourth sample S4 has a concentration of 1/1000000 of the original concentration.

As illustrated in FIG. 5, the first sample S1, the second sample S2, the third sample S3, and the fourth sample S4 are applied to the sensor array SA provided by the bio-sensing integrated circuit 100 discussed above. In some embodiments, the sensor array SA of the bio-sensing integrated circuit 100 is being divided into four regions. The first region corresponds to a first assay A1, the second region corresponds to a second assay A2, the third region corresponds to a third assay A3, and the fourth region corresponds to a fourth assay A4. In some embodiments, the first assay A1, the second assay A2, the third assay A3, and the fourth assay A4 respectively include multiple pixels PX to ensure the detection precision. In some embodiments, the first sample S1 is applied to the first assay A1, the second sample S2 is applied to the second assay A2, the third sample S3 is applied to the third assay A3, and the fourth sample S4 is applied to the fourth assay A4.

As mentioned above, depending on the concentration of the target material 400 in the samples, the target material 400 in the first sample S1, the second sample S2, the third sample S3, and the fourth sample S4 may or may not bind to the probe 300 in the respective sensing well SW (shown in FIGS. 1 and 2). In some embodiments, the binding between the target material 400 and the probe 300 would alter the conductance of the channel region 148 underneath the sensing well SW (shown in FIG. 1). This change in conductance would affect the current between the source region 144 and the drain region 146, so measuring the current between the source region 144 and the drain region 146 in each pixel PX allows the determination of the presence of the target material 400. In some embodiments, the column decoder CD provides a column selection signal to the pixels PX in the sensor array SA and the row decoder RD provides a row selection signal to the pixels PX in the sensor array SA. For example, based on the column selection signal and the row selection signal, the BioFET 100 in the selected pixel PX is turned on, and the current between the source region 144 and the drain region 146 of the BioFET 100 in the selected pixel PX is measured. Thereafter, the current between the source region 144 and the drain region 146 measured for each pixel PX is transmitted to the TIA 500 in a form of an analog signal. The TIA 500 then enhances and magnifies the analog signal received. Subsequently, the analog signal leaves the TIA 500 and is transmitted to an analog-to-digital converter (ADC) 600. The ADC 600 converts the signal received from an analog signal to a digital signal, and outputs the digital signal to a microcontroller unit (MCU) 700. In some embodiments, the MCU 700 processes the digital signal received by a software or the like. In other words, the digital signal received by MCU 700 may be standardized before being output. For example, an average of the currents between the source region 144 and the drain region 146 in the pixels PX of the same assay may be calculated, and the result output corresponds to this average value. However, the disclosure is not limited thereto. In some alternative embodiments, the digital signal received by MCU 700 may be standardized through other means. After the digital signal is being processed, the MCU 700 outputs the currents between the source region 144 and the drain region 146 for the first sample S1, the second sample S2, the third sample S3, and the fourth sample S4 as a function of time. For example, the results are shown in FIG. 6A to FIG. 6D.

In some embodiments, prior to the bio-sensing process, a limit of detection (LoD) of the bio-sensing integrated circuit 100 and a threshold current ($I_T$) related to the LoD are determined. In some embodiments, the LoD and $I_T$ may be predetermined by a calibration process or the like. By evaluating whether the output current ($I_{DS}$) between the source region 144 and the drain region 146 is below the threshold current, the threshold dilution factor and threshold sample that correspond to the LoD may be found. For example, the threshold dilution factor is the largest dilution factor that has an $I_{DS}$ above the $I_T$. Meanwhile, the threshold sample is a sample that has an $I_{DS}$ above the $I_T$ and has a lowest concentration. After obtaining the threshold dilution factor corresponding to the LoD, the initial concentration of the target material 400 in the original sample fluid may be calculated by obtaining a product of the threshold dilution factor and the LoD. For example, the initial concentration of the target material 400 in the original sample fluid may be calculated by multiplying the threshold dilution factor and LoD. In other words, the initial concentration of the target material 400 in the original sample fluid is a product of a reciprocal of the concentration of the threshold sample and the LoD. In some embodiments, the LoD ranges from about 0.1 fF/mL to about 1000 fF/mL. On the other hand, the threshold current ranges from about 0.1 μA to about 10 μA. The determination of the threshold dilution factor, the determination of the threshold sample, and the calculation of the initial concentration of the target material 400 will be exemplified below in conjunction with FIG. 6A to FIG. 6D.

FIG. 6A is a current vs. time curve of the first sample S1 in the concentration determination method of FIG. 5. FIG. 6B is a current vs. time curve of the second sample S2 in the concentration determination method of FIG. 5. FIG. 6C is a current vs. time curve of the third sample S3 in the concentration determination method of FIG. 5. FIG. 6D is a current vs. time curve of the fourth sample S4 in the concentration determination method of FIG. 5. In FIG. 6A to FIG. 6D, the time period between $t_0$ and $t_1$ denotes a period before the bio-sensing process, the time period between $t_1$ and $t_2$ denotes a period during the bio-sensing process, and the time period after $t_2$ denotes a period after the bio-sensing process.

Referring to FIG. 6A to FIG. 6C, the $I_{DS}$ for the first sample S1, the second sample S2, and the third sample S3 are all above the $I_T$ after $t_2$. On the other hand, the $I_{DS}$ for the fourth sample S4 is still below the $I_T$ after $t_2$. As mentioned above, the dilution factor $N_1$ for the first sample S1 is $10^1$, the dilution factor $N_2$ for the second sample S2 is $10^2$, and the dilution factor $N_3$ for the third sample S3 is $10^4$, so the dilution factor $N_3$ is the largest dilution factor among dilution factors $N_1$-$N_3$ that has an $I_{DS}$ above the $I_T$. Meanwhile, the third sample S3 is also the sample having the lowest concentration among the first sample S1, the second sample S2, and the third sample S3 that has an $I_{DS}$ above the $I_T$. In other words, the threshold sample in the present embodiment is the third sample S3 and the threshold dilution factor in the present embodiment is $N_3$. In the present embodiment, the LoD is predetermined as 0.1 fF/mL. Therefore, the initial concentration of the target material 400 in the original sample fluid may be calculated by multiplying 0.1 fF/mL with $10^4$, and the initial concentration of the target material 400 in the original sample fluid is found to be 1000 fF/mL.

In some embodiments, by utilizing the sensor array SA with various assays (i.e. the first assay A1, the second assay A2, the third assay A3, and the fourth assay A4) at once, one time test may be performed. As such, the testing efficiency may be sufficiently enhanced. In addition, by performing the foregoing concentration determination method, electrical signals can be easily mapped to correspond to bio-marker concentrations, and an unknown bio-marker concentration may be easily calculated.

Please be noted that although the concentration determination method shown in FIG. 5 and FIG. 6A to FIG. 6D utilizes four samples S1-S4 (i.e. the original sample is being diluted for four times), the disclosure is not limited thereto. Depending on the dilution factor selected, the sample size may vary. For example, the sample size may be ten, hundreds, thousands, or so as long as at least one of the samples renders a current between the source region 144 and the drain region 146 that is below the threshold current. In some embodiments, when the sample size is too large, one bio-sensing integrated circuit 100 may not be sufficient. As such, multiple bio-sensing integrated circuits 100 may be utilized. Meanwhile, the sensor array SA of each bio-sensing integrated circuit 100 is still being divided into multiple assays.

Figure 7:
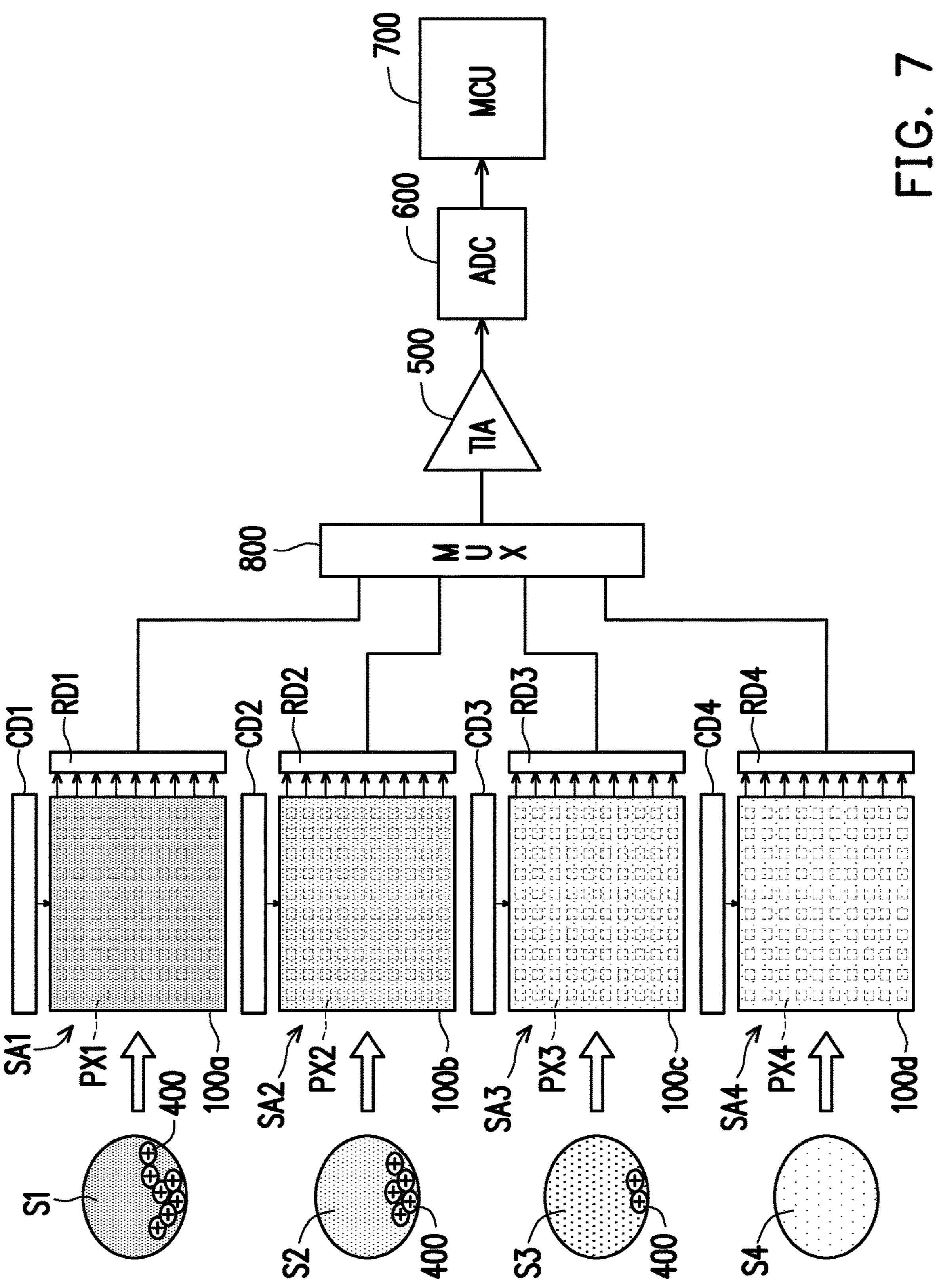
FIG. 7 is a schematic flow of a concentration determination method in accordance with some alternative embodiments of the disclosure.

FIG. 7 is a schematic flow of a concentration determination method in accordance with some alternative embodiments of the disclosure. Referring to FIG. 7, the sample fluid having the target material 400 therein is being diluted to form a first sample S1, a second sample S2, a third sample S3, and a fourth sample S4. In some embodiments, the dilution factor for the first sample S1 is $N_1$, the dilution factor for the second sample S2 is $N_2$, the dilution factor for the third sample S3 is $N_3$, and the dilution factor for the fourth sample S4 is $N_4$. In some embodiments, $N_1$ to $N_4$ may be any arbitrary positive number, as long as $N_1<N_2<N_3<N_4$. For ease of explanation, in the present embodiment, $N_1$ is taken as $10^1$, $N_2$ is taken as $10^2$, $N_3$ is taken as $10^4$, and $N_4$ is taken as $10^6$. For example, the first sample S1 has a concentration of 1/10 of the original sample fluid, the second sample S2 has a concentration of 1/100 of the original sample fluid, the third sample S3 has a concentration of 1/1000 of the original sample fluid, and the fourth sample S4 has a concentration of 1/1000000 of the original sample fluid. In some embodiments, the concentration of the target material 400 also reduces in proportional with respect to the dilution factor. For example, the target material 400 in the first sample S1 has a concentration of 1/10 of the original concentration, the target material 400 in the second sample S2 has a concentration of 1/100 of the original concentration, the target material 400 in the third sample S3 has a concentration of 1/10000 of the original concentration, and the target material 400 in the fourth sample S4 has a concentration of 1/1000000 of the original concentration.

As illustrated in FIG. 7, the first sample S1 is applied to the first sensory array SA1 provided by the first bio-sensing integrated circuit 100_a_, the second sample S2 is applied to the second sensory array SA2 provided by the second bio-sensing integrated circuit 100_b_, the third sample S3 is applied to the third sensory array SA3 provided by the third bio-sensing integrated circuit 100_c_, and the fourth sample S4 is applied to the fourth sensory array SA4 provided by the fourth bio-sensing integrated circuit 100_d_. In some embodiments, the first bio-sensing integrated circuit 100_a_, the second bio-sensing integrated circuit 100_b_, the third bio-sensing integrated circuit 100_c_, and the fourth bio-sensing integrated circuit 100_d_ are identical to one another and may be similar to the bio-sensing integrated circuit 100 in FIG. 1 and FIG. 4, so the detailed descriptions thereof are omitted herein. In some embodiments, the first bio-sensing integrated circuit 100_a_, the second bio-sensing integrated circuit 100_b_, the third bio-sensing integrated circuit 100_c_, and the fourth bio-sensing integrated circuit 100_d_ may be placed on a same cartridge. In some embodiments, the first sensor array SA1 correspond to a first assay A1, the second sensor array SA2 corresponds to a second assay A2, the third sensor array SA3 corresponds to a third assay A3, and the fourth sensor array SA4 corresponds to a fourth assay A4. In some embodiments, the first assay A1 corresponds to multiple first pixels PX1, the second assay A2 correspond to multiple second pixels PX2, the third assay A3 corresponds to multiple third pixels PX3, and the fourth assay A4 corresponds to multiple fourth pixels PX4, so as to ensure the detection precision. In some embodiments, the first sample S1 is applied to the first assay A1, the second sample S2 is applied to the second assay A2, the third sample S3 is applied to the third assay A3, and the fourth sample S4 is applied to the fourth assay A4.

As mentioned above, depending on the concentration of the target material 400 in the samples, the target material 400 in the first sample S1, the second sample S2, the third sample S3, and the fourth sample S4 may or may not bind to the probe 300 in the respective sensing well SW (shown in FIGS. 1 and 2). In some embodiments, the binding between the target material 400 and the probe 300 would alter the conductance of the channel region 148 underneath the sensing well SW (shown in FIG. 1). This change in conductance would affect the current between the source region 144 and the drain region 146, so measuring the current between the source region 144 and the drain region 146 in each pixel (i.e. the first pixel PX1, the second pixel PX2, the third pixel PX3, and the fourth pixel PX4) allows the determination of the presence of the target material 400. In some embodiments, the first column decoder CD1 provides a column selection signal to the first pixels PX1 in the first sensor array SA1 and the first row decoder RD1 provides a row selection signal to the first pixels PX1 in the first sensor array SA1. The second column decoder CD2 provides a column selection signal to the second pixels PX2 in the second sensor array SA2 and the second row decoder RD2 provides a row selection signal to the second pixels PX2 in the second sensor array SA2. The third column decoder CD3 provides a column selection signal to the third pixels PX3 in the third sensor array SA3 and the third row decoder RD3 provides a row selection signal to the third pixels PX3 in the third sensor array SA3. The fourth column decoder CD4 provides a column selection signal to the fourth pixels PX4 in the fourth sensor array SA4 and the fourth row decoder RD4 provides a row selection signal to the fourth pixels PX4 in the fourth sensor array SA4. For example, based on the column selection signal and the row selection signal, the BioFET 100 in the selected first pixel PX1, the second pixel PX2, the third pixel PX3, and the fourth pixel PX4 is turned on, and the current between the source region 144 and the drain region 146 of the BioFET 100 in the selected pixel is measured. Thereafter, the current between the source region 144 and the drain region 146 measured for each first pixel PX1, each second pixel PX2, each third pixel PX3, and each fourth pixel PX4 are transmitted to a multiplexer (MUX) 800 in a form of an analog signal. The MUX 800 then selects a particular analog signal received and forwards the selected signal to the TIA 500. The TIA 500 enhances and magnifies the analog signal received. Subsequently, the analog signal leaves the TIA 500 and is transmitted to an analog-to-digital converter (ADC) 600. The ADC 600 converts the signal received from an analog signal to a digital signal, and outputs the digital signal to a microcontroller unit (MCU) 700. In some embodiments, the MCU 700 processes the digital signal received by a software or the like. In other words, the digital signal received by MCU 700 may be standardized before being output. For example, an average of the current between the source region 144 and the drain region 146 in the first pixels PX1, an average of the current between the source region 144 and the drain region 146 in the second pixels PX2, an average of the current between the source region 144 and the drain region 146 in the third pixels PX3, and an average of the current between the source region 144 and the drain region 146 in the fourth pixels PX4 may be independently calculated, and the results output correspond to these average values. However, the disclosure is not limited thereto. In some alternative embodiments, the digital signal received by MCU 700 may be standardized through other means. After the digital signal is being processed, the MCU 700 outputs the currents between the source region 144 and the drain region 146 for the first sample S1, the second sample S2, the third sample S3, and the fourth sample S4 as a function of time. For example, the results are shown in FIG. 8A to FIG. 8D.

In some embodiments, prior to the bio-sensing process, a limit of detection (LoD) of the first bio-sensing integrated circuit 100*a*, the second bio-sensing integrated circuit 100*b*, the third bio-sensing integrated circuit 100*c*, and the fourth bio-sensing integrated circuit 100*d* are determined. Meanwhile, a threshold current ($I_T$) related to the LoD is also determined. In some embodiments, the LoD and $I_T$ may be predetermined by a calibration process or the like. In some embodiments, the LoD of the first bio-sensing integrated circuit 100*a*, the second bio-sensing integrated circuit 100*b*, the third bio-sensing integrated circuit 100*c*, and the fourth bio-sensing integrated circuit 100*d* are identical. By evaluating whether the output current ($I_{DS}$) between the source region 144 and the drain region 146 is below the threshold current, the threshold dilution factor and the threshold sample that correspond to the LoD may be found. For example, the threshold dilution factor is the largest dilution factor that has an $I_{DS}$ above the $I_T$. Meanwhile, the threshold sample is a sample that has an $I_{DS}$ above the $I_T$ and has a lowest concentration. After obtaining the threshold dilution factor corresponding to the LoD, the initial concentration of the target material 400 in the original sample fluid may be calculated by obtaining a product of the threshold dilution factor and the LoD. For example, the initial concentration of the target material 400 in the original sample fluid may be calculated by multiplying the threshold dilution factor and LoD. In other words, the initial concentration of the target material 400 in the original sample fluid is a product of a reciprocal of the concentration of the threshold sample and the LoD. In some embodiments, the LoD ranges from about 0.1 fF/mL to about 1000 fF/mL. On the other hand, the threshold current ranges from about 0.1 μA to about 10 μA. The determination of the threshold dilution factor, the determination of the threshold sample, and the calculation of the initial concentration of the target material 400 will be exemplified below in conjunction with FIG. 8A to FIG. 8D.

FIG. 8A is a current vs. time curve of the first sample S1 in the concentration determination method of FIG. 7. FIG. 8B is a current vs. time curve of the second sample S2 in the concentration determination method of FIG. 7. FIG. 8C is a current vs. time curve of the third sample S3 in the concentration determination method of FIG. 7. FIG. 8D is a current vs. time curve of the fourth sample S4 in the concentration determination method of FIG. 7. In FIG. 8A to FIG. 8D, the time period between $t_0$ and $t_1$ denotes a period before the bio-sensing process, the time period between $t_1$ and $t_2$ denotes a period during the bio-sensing process, and the time period after $t_2$ denotes a period after the bio-sensing process.

Referring to FIG. 8A to FIG. 8C, the $I_{DS}$ for the first sample S1, the second sample S2, and the third sample S3 are all above the $I_T$ after $t_2$. On the other hand, the $I_{DS}$ for the fourth sample S4 is still below the $I_T$ after $t_2$. As mentioned above, the dilution factor $N_1$ for the first sample S1 is $10^1$, the dilution factor $N_2$ for the second sample S2 is $10^2$, and the dilution factor $N_3$ for the third sample S3 is $10^4$, so the dilution factor $N_3$ is the largest dilution factor among dilution factors $N_1$-$N_3$ that has an $I_{DS}$ above the $I_T$. Meanwhile, the third sample S3 is also the sample having the lowest concentration among the first sample S1, the second sample S2, and the third sample S3 that has an $I_{DS}$ above the $I_T$. In other words, the threshold sample in the present embodiment is the third sample S3 and the threshold dilution factor in the present embodiment is $N_3$. In the present embodiment, the LoD is predetermined as 0.1 fF/mL. Therefore, the initial concentration of the target material 400 in the original sample fluid may be calculated by multiplying 0.1 fF/mL with $10^4$, and the initial concentration of the target material 400 in the original sample fluid is found to be 1000 fF/mL.

In some embodiments, by utilizing the different sensor arrays (i.e. the first sensor array SA1, the second sensor array SA2, the third sensor array SA3, and the fourth sensor array SA4) with various assays (i.e. the first assay A1, the second assay A2, the third assay A3, and the fourth assay A4) at once, one time test may be performed. As such, the testing efficiency may be sufficiently enhanced. In addition, by performing the foregoing concentration determination method, electrical signals can be easily mapped to correspond to bio-marker concentrations, and an unknown bio-marker concentration may be easily calculated.

Please be noted that although the concentration determination method shown in FIG. 7 and FIG. 8A to FIG. 8D utilizes four samples S1-S4 (i.e. the original sample is being diluted for four times), the disclosure is not limited thereto. Depending on the dilution factor selected, the sample size may vary. For example, the sample size may be ten, hundreds, thousands, or so as long as at least one of the samples renders a current between the source region 144 and the drain region 146 that is below the threshold current.

In accordance with some embodiments of the disclosure, a concentration determination method includes at least the following steps. A sample fluid having a target material therein is diluted with a $1^{st}$ dilution factor to an $N^{th}$ dilution factor to respectively form a $1^{st}$ sample to an $N^{th}$ sample. The $N^{th}$ dilution factor is greater than the $N^{th-1}$ dilution factor. A bio-sensing integrated circuit having a sensor array is provided. The sensor array is divided into a $1^{st}$ assay to an $N^{th}$ assay. The $1^{st}$ sample to the $N^{th}$ sample are respectively applied to the $1^{st}$ assay to the $N^{th}$ assay. A bio-sensing process is performed on the $1^{st}$ sample to the $N^{th}$ sample by the bio-sensing integrated circuit to obtain a $1^{st}$ measurement value to an $N^{th}$ measurement value respectively for the $1^{st}$ sample to the $N^{th}$ sample. The $1^{st}$ measurement value to the $N^{th}$ measurement value are compared with a threshold value to determine a threshold dilution factor. The threshold dilution factor corresponds to a largest dilution factor that has a measurement value higher than the threshold value. A concentration of the target material in the sample fluid is calculated based on the threshold dilution factor and a limit of detection of the bio-sensing integrated circuit.

In accordance with some alternative embodiments of the disclosure, a concentration determination method includes at least the following steps. A sample fluid having a target material therein is diluted with a $1^{st}$ dilution factor to an $N^{th}$ dilution factor to respectively form a $1^{st}$ sample to an $N^{th}$ sample. The $N^{th}$ dilution factor is greater than the $N^{th-1}$ dilution factor. A $1^{st}$ bio-sensing integrated circuit to an $N^{th}$ bio-sensing integrated circuit are provided. The $1^{st}$ sample to the $N^{th}$ sample are respectively applied onto the $1^{st}$ bio-sensing integrated circuit to the $N^{th}$ bio-sensing integrated circuit. A bio-sensing process is performed on the $1^{st}$ sample to the $N^{th}$ sample by the $1^{st}$ bio-sensing integrated circuit to the $N^{th}$ bio-sensing integrated circuit to obtain a $1^{st}$ measurement value to an $N^{th}$ measurement value respectively for the $1^{st}$ sample to the $N^{th}$ sample. The $1^{st}$ measurement value to the $N^{th}$ measurement value are compared with a threshold value to determine a threshold dilution factor. The threshold dilution factor corresponds to a largest dilution factor that has a measurement value higher than the threshold value. A concentration of the target material in the sample fluid is calculated based on the threshold dilution factor and limit of detections of the $1^{st}$ bio-sensing integrated circuit to the $N^{th}$ bio-sensing integrated circuit.

In accordance with some alternative embodiments of the disclosure, a concentration determination method includes at least the following steps. A $1^{st}$ sample to an $N^{th}$ sample respectively having a concentration of $1/N_1$ to $1/N_{th}$ of a sample fluid is provided. The concentration decreases from the $1^{st}$ sample to the $N^{th}$ sample. The $1^{st}$ sample to the $N^{th}$ sample are respectively applied onto a $1^{st}$ assay to an $N^{th}$ assay. A bio-sensing process is performed on the $1^{st}$ sample to the $N^{th}$ sample by a bio-sensing integrated circuit to obtain a $1^{st}$ measurement value to an $N^{th}$ measurement value respectively for the $1^{st}$ sample to the $N^{th}$ sample. The $1^{st}$ measurement value to the $N^{th}$ measurement value are compared with a threshold value to determine a threshold sample. The threshold sample corresponds to a sample that has a measurement value higher than the threshold value and has a lowest concentration. A concentration of the target material in the sample fluid is calculated based on the concentration of the threshold sample and a limit of detection of the bio-sensing integrated circuit.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A concentration determination method, comprising:

diluting a sample fluid having a target material therein with a $1^{st}$ dilution factor to an $N^{th}$ dilution factor to respectively form a $1^{st}$ sample to an $N^{th}$ sample, wherein the $N^{th}$ dilution factor is greater than the $N^{th-1}$ dilution factor;

providing a bio-sensing integrated circuit having a sensor array, wherein the sensor array is divided into a $1^{st}$ assay to an $N^{th}$ assay;

respectively applying the $1^{st}$ sample to the $N^{th}$ sample onto the $1^{st}$ assay to the $N^{th}$ assay;

performing a bio-sensing process on the $1^{st}$ sample to the $N^{th}$ sample by the bio-sensing integrated circuit during a time period between a first time $t_1$ and a second time $t_2$ to obtain a $1^{st}$ measurement value to an $N^{th}$ measurement value at the second time $t_2$ respectively for the $1^{st}$ sample to the $N^{th}$ sample through the $1^{st}$ assay to the $N^{th}$ assay;

converting the $1^{st}$ measurement value to the $N^{th}$ measurement value to digital signals through a Trans-impedance Amplifier (TIA) and an analog-to-digital converter (ADC);

comparing the digital signals with a threshold value and evaluating which one of the digital signals is below the threshold value, by a microcontroller unit (MCU), to determine a threshold dilution factor, wherein the threshold dilution factor corresponds to a largest dilution factor that has a measurement value higher than the threshold value, wherein the threshold value ranges from about 0.1 μA to about 10 μA; and calculating a concentration of the target material in the sample fluid based on the threshold dilution factor and a limit of detection of the bio-sensing integrated circuit.

2. The method of claim 1, wherein the concentration of the target material in the sample fluid is a product of the threshold dilution factor and the limit of detection of the bio-sensing integrated circuit.

3. The method of claim 1, wherein the bio-sensing integrated circuit comprises Biosensor Field-Effect Transistors (BioFETs), the sensory array comprises pixels arranged in an array, and each BioFET corresponds to a pixel.

4. The method of claim 3, wherein each BioFET comprises a drain region and a source region, and the $1^{st}$ measurement value to the $N^{th}$ measurement value are currents between the source region and the drain region.

5. The method of claim 4, wherein the first measurement value is an average value of the currents between the source region and the drain region of each pixel in the $1^{st}$ assay of the sensor array.

6. The method of claim 3, wherein the bio-sensing integrated circuit comprises sensing wells located directly above each BioFET, and each sensing well corresponds to a pixel.

7. The method of claim 6, wherein during the bio-sensing process, a probe is provided in one of the sensing wells, and the target material is bind to the probe.

8. The method of claim 1, wherein the target material comprises SAS-COV-2 Antigen, SARS-COV-2 Antibody, or SARS-COV-2 RNA.

9. A concentration determination method, comprising:

diluting a sample fluid having a target material therein with a $1^{st}$ dilution factor to an $N^{th}$ dilution factor to respectively form a $1^{st}$ sample to an $N^{th}$ sample, wherein the $N^{th}$ dilution factor is greater than the $N^{th-1}$ dilution factor;

providing a $1^{st}$ bio-sensing integrated circuit to an $N^{th}$ bio-sensing integrated circuit, wherein the $1^{st}$ bio-sensing integrated circuit to the $N^{th}$ bio-sensing integrated circuit respectively comprise a $1^{st}$ sensory array to an $N^{th}$ sensory array;

respectively applying the $1^{st}$ sample to the $N^{th}$ sample onto the $1^{st}$ bio-sensing integrated circuit to the $N^{th}$ bio-sensing integrated circuit;

performing a bio-sensing process on the $1^{st}$ sample to the $N^{th}$ sample by the $1^{st}$ sensory array to the $N^{th}$ sensory array of the $1^{st}$ bio-sensing integrated circuit to the $N^{th}$ bio-sensing integrated circuit during a time period between a first time $t_1$ and a second time $t_2$ to obtain a $1^{st}$ measurement value to an $N^{th}$ measurement value at the second time $t_2$ respectively for the $1^{st}$ sample to the $N^{th}$ sample;

converting the $1^{st}$ measurement value to the $N^{th}$ measurement value to digital signals through a Trans-impedance Amplifier (TIA) and an analog-to-digital converter (ADC);

comparing the digital signals with a threshold value and evaluating which one of the digital signals is below the threshold value, by a microcontroller unit (MCU), to determine a threshold dilution factor, wherein the threshold dilution factor corresponds to a largest dilution factor that has a measurement value higher than the threshold value, wherein the threshold value ranges from about 0.1 μA to about 10 μA; and calculating a concentration of the target material in the sample fluid based on the threshold dilution factor and limit of detections of the $1^{st}$ bio-sensing integrated circuit to the $N^{th}$ bio-sensing integrated circuit.

10. The method of claim 9, wherein the limitation of detections of the $1^{st}$ bio-sensing integrated circuit to the $N^{th}$ bio-sensing integrated circuit are identical.

11. The method of claim 10, wherein the concentration of the target material in the sample fluid is a product of the threshold dilution factor and the limit of detections.

12. The method of claim 9, wherein each of the $1^{st}$ bio-sensing integrated circuit to the $N^{th}$ bio-sensing integrated circuit respectively comprises Biosensor Field-Effect Transistors (BioFETs), each BioFET comprises a drain region and a source region, and the $1^{st}$ measurement value to the $N^{th}$ measurement value are currents between the source region and the drain region of each BioFET.

13. The method of claim 12, wherein the first measurement value is an average value of the currents between the source region and the drain region of each BioFET in the $1^{st}$ bio-sensing integrated circuit.

14. The method of claim 9, wherein the $1^{st}$ bio-sensing integrated circuit to the $N^{th}$ bio-sensing integrated circuit are placed on a same cartridge.

15. The method of claim 9, wherein the target material comprises SAS-COV-2 Antigen, SARS-COV-2 Antibody, or SARS-COV-2 RNA.

16. A concentration determination method, comprising:

providing a $1^{st}$ sample to an $N^{th}$ sample respectively having a concentration of $1/N_1$ to $1/N^{th}$ of a sample fluid, wherein the concentration decreases from the 1st sample to the $N^{th}$ sample;

respectively applying the $1^{st}$ sample to the $N^{th}$ sample onto a $1^{st}$ assay to an $N^{th}$ assay;

performing a bio-sensing process on the $1^{st}$ sample to the $N^{th}$ sample by a bio-sensing integrated circuit having the $1^{st}$ assay to the $N^{th}$ assay during a time period between a first time $t_1$ and a second time $t_2$ to obtain a $1^{st}$ measurement value to an $N^{th}$ measurement value at the second time $t_2$ respectively for the $1^{st}$ sample to the $N^{th}$ sample;

converting the $1^{st}$ measurement value to the $N^{th}$ measurement value to digital signals through a Trans-impedance Amplifier (TIA) and an analog-to-digital converter (ADC);

comparing the digital signals with a threshold current and evaluating which one of the digital signals is below the threshold current, by a microcontroller unit (MCU), to determine a threshold dilution factor, wherein the threshold dilution factor corresponds to a largest dilution factor that has a measurement value higher than the threshold current, wherein the threshold current ranges from about 0.1 μA to about 10 μA; and calculating a concentration of the target material in the sample fluid based on the threshold dilution factor and a limit of detection of the bio-sensing integrated circuit.

17. The method of claim 16, wherein the concentration of the target material in the sample fluid is a product of the threshold dilution factor and the limit of detection of the bio-sensing integrated circuit.

18. The method of claim 16, wherein the bio-sensing integrated circuit comprises Biosensor Field-Effect Transistors (BioFETs), each BioFET comprises a drain region and a source region, and the $1^{st}$ measurement value to the $N^{th}$ measurement value are currents between the source region and the drain region of each BioFET.

19. The method of claim 18, wherein the first measurement value is an average value of the currents between the source region and the drain region of each BioFET in the $1^{st}$ assay.

20. The method of claim 16, wherein the target material comprises SAS-COV-2 Antigen, SARS-COV-2 Antibody, or SARS-COV-2 RNA.

* * * * *